(12) United States Patent
Nose et al.

(10) Patent No.: US 7,430,905 B2
(45) Date of Patent: Oct. 7, 2008

(54) LEG STRENGTH CALCULATION DEVICE, LEG STRENGTH CALCULATION METHOD, AND PROGRAM

(75) Inventors: Hiroshi Nose, Azumino (JP); Hirokazu Genno, Hirakata (JP); Yoshinori Tanabe, Hirakata (JP)

(73) Assignees: Sanyo Electric Co., Ltd., Moriguchi (JP); Non-Profit Organization Jukunen Taiiku Daigaku Research Center, Matsumoto (JP)

( * ) Notice: Subject to any disclaimer, the term of this patent is extended or adjusted under 35 U.S.C. 154(b) by 146 days.

(21) Appl. No.: 11/307,946

(22) Filed: Feb. 28, 2006

(65) Prior Publication Data
US 2006/0191335 A1    Aug. 31, 2006

(30) Foreign Application Priority Data
Feb. 28, 2005   (JP) ............................ P2005-055221
Feb. 13, 2006   (JP) ............................ P2006-035835

(51) Int. Cl.
*A61B 5/22*   (2006.01)

(52) U.S. Cl. .................................................. 73/379.01
(58) Field of Classification Search .............. 73/379.01, 73/818, 379, 514.16
See application file for complete search history.

(56) References Cited

U.S. PATENT DOCUMENTS

2006/0053897 A1 *   3/2006   Kuivala et al. ................ 73/818

FOREIGN PATENT DOCUMENTS

| JP | 2000-101139 | | 4/2000 |
|----|-------------|---|--------|
| JP | 2002-209874 | | 7/2002 |
| JP | 2004-266240 | | 9/2004 |
| JP | 02006320533 | A * | 11/2006 |

* cited by examiner

*Primary Examiner*—Jewel V Thompson
(74) *Attorney, Agent, or Firm*—NDQ&M Watchstone LLP; Vincent M. DeLuca (57) ABSTRACT

An acceleration sensor measures accelerations of the subject which act in directions of axes x, y, and z orthogonal to each other when the subject walks. A leg strength calculation unit calculates leg strength of the subject based on values of the accelerations measured by the acceleration sensor.

27 Claims, 9 Drawing Sheets

LEG STRENGTH CALCULATION DEVICE, LEG STRENGTH CALCULATION METHOD, AND PROGRAM

CROSS REFERENCE TO RELATED APPLICATIONS

This application is based upon and claims the benefit of priority from the prior Japanese Patent Applications No. P2005-055221, filed on Feb. 28, 2005: P2006-35835, filed on Feb. 13, 2006; the entire contents of which are incorporated herein by reference.

BACKGROUND OF THE INVENTION

1. Field of the Invention

The present invention relates to a leg strength calculation device which is detachably worn by a subject and calculates leg strength of the subject, a leg strength calculation method, and a program.

2. Description of the Related Art

Exercise equipment which calculates leg strength of a subject has hitherto been proposed (for example, see Japanese Patent Laid-open Publication No. 2002-209874). This exercise equipment includes a rail extended in a predetermined direction, a plate slidably supported on the rail, and a seat on which a subject sits. The subject sits on the seat with his/her legs bent and his/her feet against the plate and strongly pushes his/her feet forward.

The exercise equipment therefore detects load acting on the plate pushed by the feet of the subject and calculates the leg strength of the subject based on the detected load.

BRIEF SUMMARY OF THE INVENTION

However, with the aforementioned exercise equipment, the subject needs to instantaneously push the feet forward with his/her feet against the plate at maximum strength that the subject has. This places a burden on particularly elderly persons.

Moreover, the aforementioned exercise equipment is large in size and expensive. Accordingly, the subject cannot easily know the leg strength with this exercise equipment.

The present invention is made in the light of the above points, and an object of the present invention is to provide a leg strength calculation device, a leg strength method, and a program capable of easily calculating leg strength of a subject without placing a heavy burden on the subject.

To solve the aforementioned problems, the present invention includes the following characteristics. A first aspect of the present invention is a leg strength calculation device detachably worn by a subject, including: an acceleration sensor configured to measure accelerations of the subject which act in directions of axes x, y, and z orthogonal to each other when the subject walks; and a leg strength calculation unit configured to calculate leg strength of the subject based on values of the accelerations measured by the acceleration sensor. The leg strength calculation device, leg strength calculation method, and program are provided with same operations and effects as those shown below.

According to the first aspect of the present invention, the leg strength of the subject corresponding to the values of accelerations is calculated based on the values of accelerations acting on the subject.

It is therefore possible to calculate the leg strength of the subject only by the subject's walking or the like without using exercise equipment which places a heavy burden on the subject to calculate the leg strength of the subject.

A second aspect of the present invention is that: the axis z is an axis in a vertical direction; the leg strength calculation unit calculates, based on a ratio of a first acceleration value to a second acceleration value, the leg strength of the subject corresponding to the ratio; the first acceleration value which is a value of the acceleration acting in the direction of the axis z measured by the acceleration sensor; and the second acceleration value which is a composite value of the accelerations acting in the directions of the axes x, y, and z measured by the acceleration sensor.

A third aspect of the present invention is that: the leg strength calculation unit calculates the leg strength of the subject corresponding to a ratio of the first acceleration value to the second acceleration value based on an approximate expression which is obtained based on a relation between a specific ratio and leg strength of the large number of subjects; and the specific ratio is a ratio of an acceleration acting in the direction of the axis z to a composite value of accelerations acting in the directions of the axes x, y, and z of a large number of subjects.

A fourth aspect of the present invention is that: the leg strength calculation unit calculates, based on a ratio of the first acceleration value to the second acceleration value when the second acceleration value is larger than a threshold value, the leg strength of the subject corresponding to the ratio.

A fifth aspect of the present invention is that: the leg strength calculation unit calculates, based on a specific value, the leg strength of the subject corresponding to the specific value; and the specific value is a composite value of accelerations acting in the directions of the axes x, y, and z measured by the acceleration sensor.

A sixth aspect of the present invention is that: the leg strength calculation unit calculates, based on a specific value, the leg strength of the subject corresponding to the specific value; and the specific value which includes weight of the subject and a composite value of accelerations acting in the directions of the axes x, y, and z measured by the acceleration sensor.

A seventh aspect of the present invention is that: the leg strength calculation unit calculates the leg strength of the subject corresponding to the specific value based on an approximate expression which is obtained based on a relation between the specific value of a number of subjects and leg strength of the number of subjects.

An eighth aspect of the present invention is that: the leg strength calculation unit calculates the leg strength of the subject corresponding to the specific value when the specific value measured is larger than a threshold value.

A ninth aspect of the present invention is that: the leg strength calculation unit calculates a composite value at maximum exercise intensity based on a measurement composite value; the composite value at maximum exercise intensity is a composite value of the accelerations acting in the directions of the axes x, y, and z when the subject can exert maximum exercise intensity that the subject can; the measurement composite value is a composite value of the accelerations acting in the directions of the axes of x, y, and z measured by the acceleration sensor.

DETAILED DESCRIPTION OF THE INVENTION

First Embodiment (External View of Leg Strength Calculation Device)

Figure 1A:
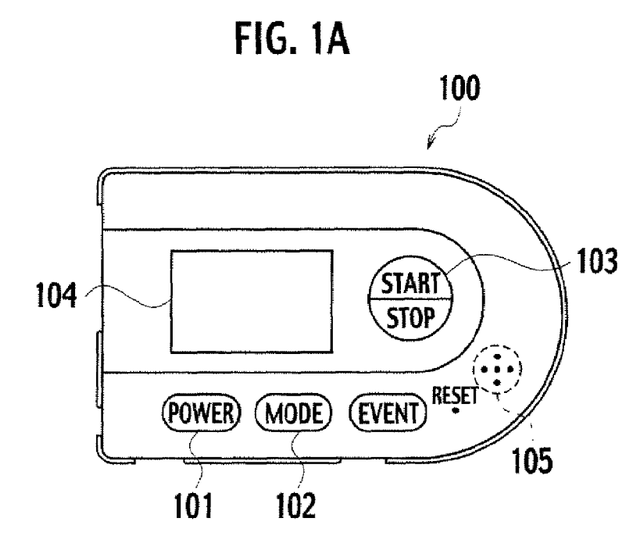
FIGS. 1A and 1B are external views showing a leg strength calculation device according to a first embodiment.
Figure 1B:
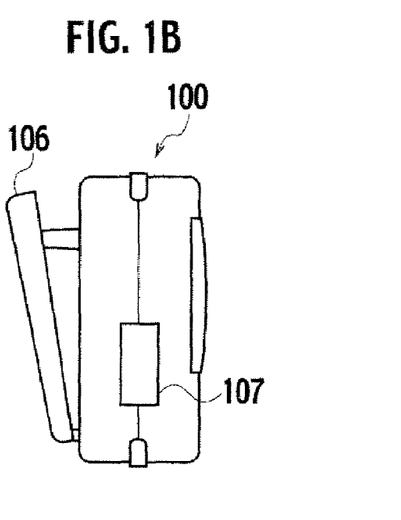

A description is given of a first embodiment with reference to the drawings. FIGS. 1A and 1B are views showing an appearance of a leg strength calculation device 100 according to the embodiment. FIGS. 1A and 1B are views showing a front face and a side face of the leg strength calculation device 100, respectively.

The leg strength calculation device 100 is detachably worn by a subject. The leg strength calculation device 100 measures quantities of exercise of the subject wearing the leg strength calculation device 100, such as leg strength (leg extension strength, leg flexion strength), the number of steps, caloric expenditure, and endurance. The leg strength is leg muscular strength.

As shown in FIG. 1A, in the front face of the leg strength calculation equipment 100, a power button 101, a mode change button 102, a start button 103, a display unit 104, and a speaker 105 are provided.

The power button 101 is used to turn the leg strength calculation device 100 on and off. The mode change button 102 is used to shift the leg strength calculation device 100 into any one of modes including a mode to calculate the endurance of the subject (hereinafter, just referred to as an endurance mode), a mode to cause the subject to execute an exercise according to physical strength of the subject (herein after, just referred to as a training mode), and a mode to calculate leg strength of the subject (hereinafter, just referred to as a leg strength mode).

The start button 103 is used to input start and stop of measurements of the quantities of exercise. The display unit 104 displays the quantities of exercise such as the calculated leg strength, number of steps, endurance, and caloric expenditure. The speaker 105 outputs a sound to change walking speed of the subject.

As shown in FIG. 1B, a clip 106 is provided in a rear face of the leg strength calculation device 100. A communication port 107 is provided in the side face of the leg strength calculation device 100. The clip 106 is used to wear the leg strength calculation device 100 on clothes of the subject. The communication port 107 can be connected to a personal computer and the like.

Figure 2A:
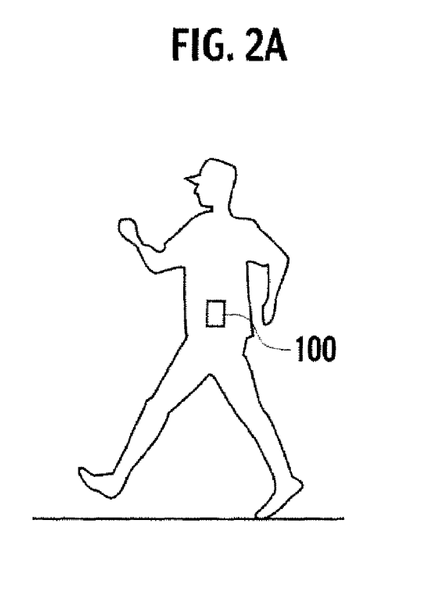
FIGS. 2A and 2B are views showing directions of accelerations acting on the leg strength calculation device according to the first embodiment.
Figure 2B:
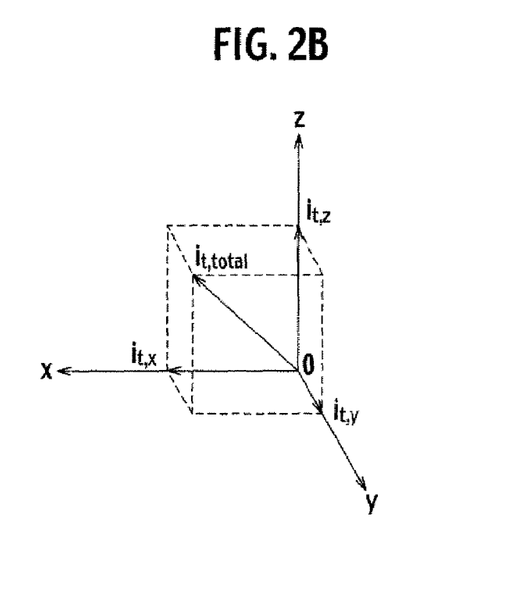

FIG. 2A is a view showing the leg strength calculation device 100 of this embodiment worn by the subject. FIG. 2B is a view showing directions of accelerations acting on the subject.

As shown in FIG. 2A, the leg strength calculation device 100 is worn on a subject's body or the like. As shown in FIG. 2B, when the leg strength calculation device 100 is worn by the subject, accelerations act on the leg strength calculation device 100 in directions of three axes orthogonal to each other. Specifically, accelerations act on the leg strength calculation device 100 in directions of an axis x (herein, an axis in a direction that the subject advances), an axis y (herein, an axis in a lateral direction of the subject), and an axis z (herein, an axis in a vertical direction).

(Internal Block Structure of Leg Strength Calculation Device)

Figure 3:
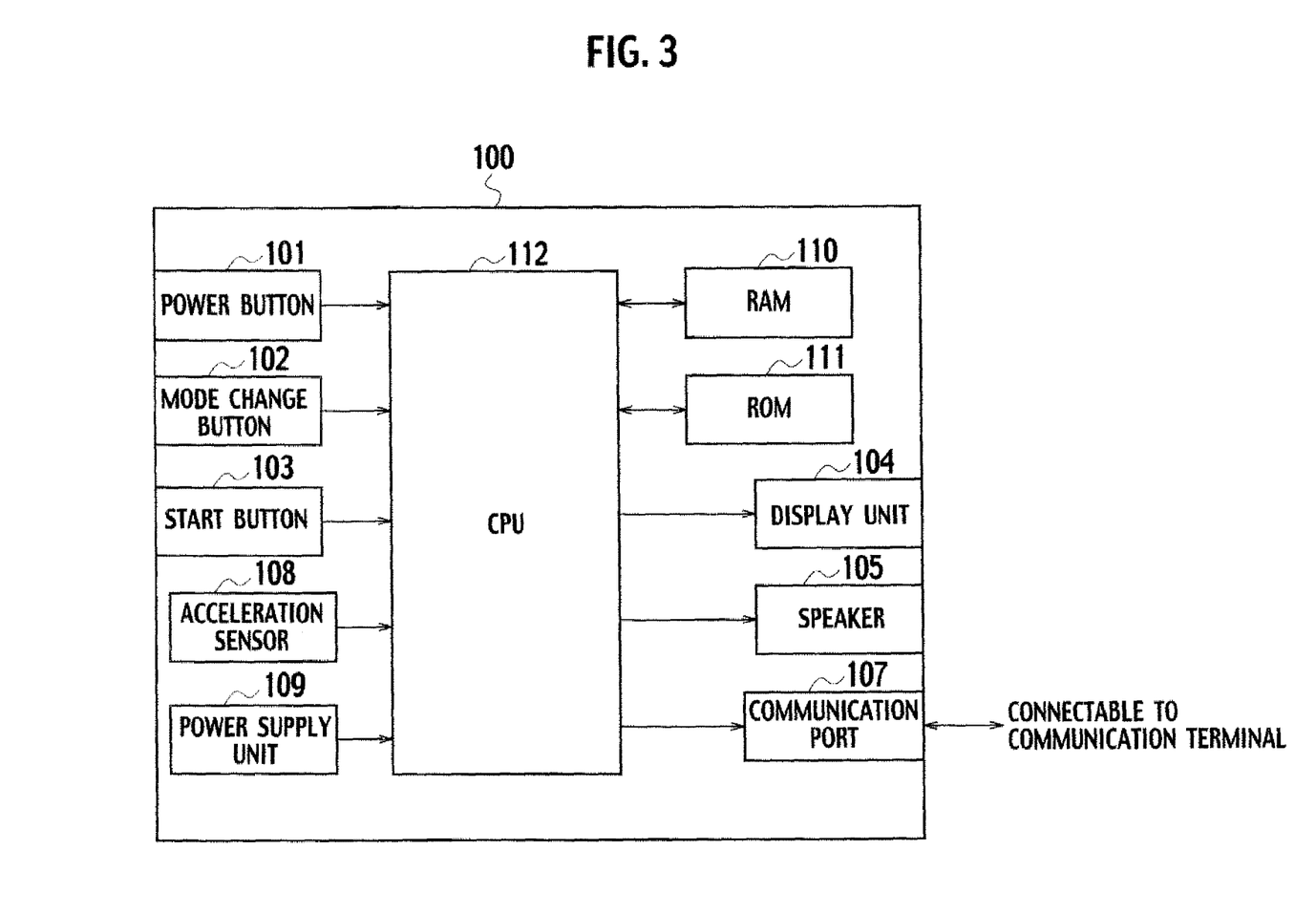
FIG. 3 is a block diagram showing an internal structure of the leg strength calculation device according to the first embodiment.

Next, referring to FIG. 3, a description is given of an internal block structure of the leg strength calculation device 100. FIG. 3 is a diagram showing the internal block structure of the leg strength calculation device 100 of this embodiment.

As shown in FIG. 3, the leg strength calculation device 100 includes the power button 101, the mode change button 102, the start button 103, the display unit 104, the speaker 105, the communication port 107, an acceleration sensor 108, a power supply unit 109, a RAM 110, a ROM 111, and a CPU 112.

The power button 101, mode change button 102, start button 103, display unit 104, and speaker 105 are used as interfaces between the leg strength calculation device 100 and the subject as described above.

The communication port 107 is a communication interface allowing the leg strength calculation device 100 to be connected to a personal computer and the like. Examples of the communication port 107 include the Universal Serial Bus (USB).

The personal computer connected through the communication port 107 can perform reception of measurement data of the quantities of exercise stored in the RAM 110, update of a program to execute an internal operation of the leg strength calculation device 100, the program being stored in the RAM 110, and the like.

The personal computer can set weight of the subject and the like in the RAM 110.

The acceleration sensor 108 measures accelerations of the subject walking. In this embodiment, the acceleration sensor 108 measures accelerations in the directions of the three axes orthogonal to each other (see Equation 1 described later). Specifically, the acceleration sensor 108 measures the accelerations of the subject acting in the directions of the axes x, y, and z.

The power supply unit 109 supplies power to operate the internal blocks. The RAM 110 temporarily stores data processed by the CPU 112. The RAM 110 can store data necessary for processing, such as the weight of the subject.

The ROM 111 stores a program to operate the internal blocks and the like.

The CPU 112 calculates leg strength of the subject based on values of the accelerations measured by the acceleration sensor 108. In this embodiment, the CPU 112 calculates, based on a ratio of a first acceleration value ($i_z$ described later) to a second acceleration value ($i_o$ described later), leg strength of the subject corresponding with the ratio (see a leg strength mode process shown in FIG. 5 described later). The first acceleration value is a value of the acceleration acting in the direction of the axis z and measured by the acceleration sensor 108. The second acceleration value is a composite value of the accelerations acting in the directions of the axes x, y, and z and measured by the acceleration sensor 108. The CPU 112 constitutes a leg strength calculation unit.

The CPU 112 calculates the leg strength of the subject corresponding with the ratio of the first acceleration value to the second acceleration value based on an approximate expression (see the later-described leg strength mode process shown in FIG. 5 and a later-described leg strength-$I'_z/I'_{total}$ property calculation process shown in FIG. 9). This approximate expression is obtained in advance from a relation between a ratio of a large number of subjects and leg strength of the large number of subjects. The ratio is a ratio of the acceleration acting in the z-axis direction to a composite value of the accelerations acting in the directions of the axes x, y, and z.

Moreover, the CPU 112 calculates, based on the ratio of the first acceleration value to the second acceleration value when the second acceleration value is larger than a threshold value, leg strength of the subject corresponding with the ratio (see the later-described leg strength mode process shown in FIG. 5).

(Leg Strength Calculation Method)

Figure 4:
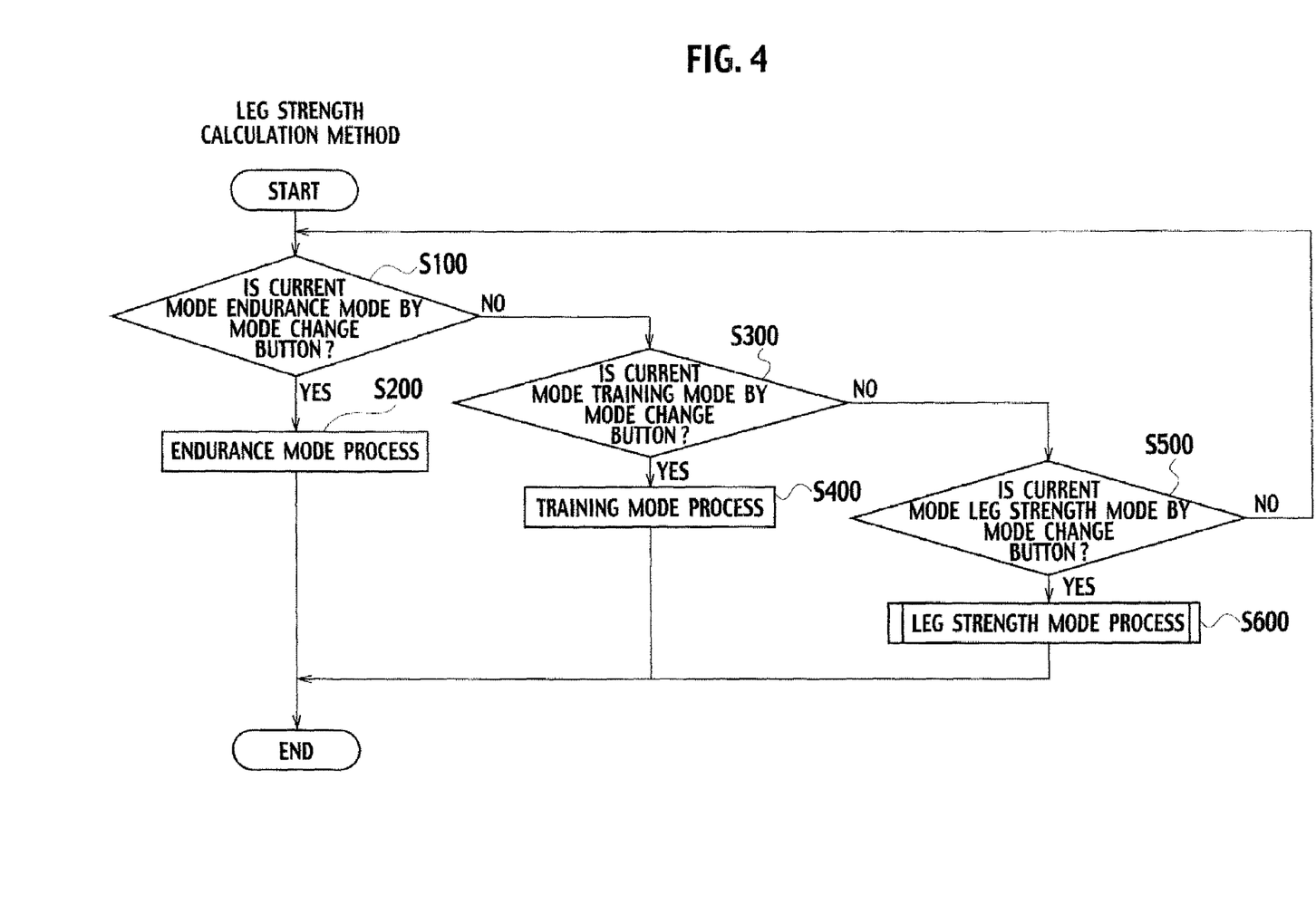
FIG. 4 is a flowchart showing a leg strength calculation method according to the first embodiment.

Next, a description is given of a leg strength calculation method as an operation of the leg strength calculation device 100 with reference to FIGS. 4 to 8. FIG. 4 is a flowchart showing the leg strength calculation method.

As shown in FIG. 4, in S100, the leg strength calculation device 100 judges whether a current mode is the endurance mode by the mode change button 102. The leg strength calculation device 100 proceeds to a process of S200 when the judgment is YES and proceeds to a process of S300 when the judgment is NO.

In S200, the leg strength calculation device 100 executes the endurance mode process to calculate the endurance of the subject.

Specifically, first, the leg strength calculation device 100 causes the speaker 105 at each predetermined time to output walking information (for example, beeps) prompting the subject to autonomously walk faster at a current time than at a previous time. The leg strength calculation device 100 causes the speaker 105 at a final time to output fastest walking information (for example, quick beeps). The fastest walking information is an information prompting the subject to walk at a maximum speed at which the subject can walk.

After causing the speaker 105 to output the fastest walking information, the leg strength calculation device 100 calculates a maximum value of impulse of the subject based on the accelerations acting on the subject. Based on a maximum impulse-maximum oxygen uptake property set in advance, the leg strength calculation device 100 calculates a maximum oxygen uptake (endurance) corresponding to the calculated maximum value of the impulse.

The endurance of the subject can be thus calculated only by the subject autonomously walking at the maximum speed. The subject can therefore easily know the endurance of the subject without using exercise equipment which places a heavy burden on the subject to calculate the endurance of the subject, such as an ergometer.

The leg strength calculation device 100 measures, for example, an exercise intensity (for example, the pulse rate, heart rate, caloric expenditure, or oxygen uptake) indicating an intensity of the exercise while the subject is walking. After causing the speaker 105 to output the fastest walking information, the leg strength calculation device 100 specifies a maximum value of the exercise intensity in a predetermined period of time.

The leg strength calculation device 100 specifies a value of acceleration acting on the subject (for example, a measurement composite value which is a composite value of the accelerations acting in the directions of the axes x, y, and z) at the time when the exercise intensity takes the maximum value.

The leg strength calculation device 100 can therefore calculate the maximum value of the impulse of the subject (which corresponds to $I''_{total}$ later described) using the specified value of acceleration. Moreover, based on the maximum value of the impulse and an previously set approximate expression for the maximum impulse-maximum oxygen uptake (endurance) property, the leg strength calculation device 100 can calculate the maximum oxygen uptake (endurance) corresponding to the maximum value of impulse.

The endurance of the subject can be thus calculated only by the subject increasing the walking speed stepwise and walking at the maximum speed in a final stage. The subject can therefore easily know the endurance of the subject without using exercise equipment which places a heavy burden on the subject to calculate the endurance of the subject, such as an ergometer.

In S300, the leg strength calculation device 100 judges whether the current mode is the training mode by the mode change button 102. The leg strength calculation device 100 proceeds to S400 when the judgment is YES and proceeds to S500 when the judgment is NO.

In S400, the leg strength calculation device 100 executes a training mode process causing the subject to execute an exercise according to physical strength of the subject. Specifically, the leg strength calculation device 100 causes the speaker 105 to alternately output normal walking information and the fastest walking information at each predetermined time. The normal walking information is information prompting the subject to autonomously walk at normal speed, and the fastest walking information is information prompting the subject to autonomously walk at the maximum speed.

This enables the subject to alternately execute walking at the normal speed and walking at the maximum speed. The subject can therefore improve in leg strength, endurance, and the like more effectively than only by walking at the normal speed.

In S500, the leg strength calculation device 100 judges whether the current mode is the leg strength mode by the mode change button 102. The leg strength calculation device 100 proceeds to a process of S600 when the judgment is YES and proceeds to the process of S100 when the judgment is NO.

In S600, the leg strength calculation device 100 executes a leg strength mode process to calculate the leg strength of the subject. This leg strength mode process is described in detail with FIG. 5.

Next, the leg strength mode process is described with reference to FIGS. 5 to 8. FIG. 5 is a flowchart showing the leg strength mode process.

Figure 5:
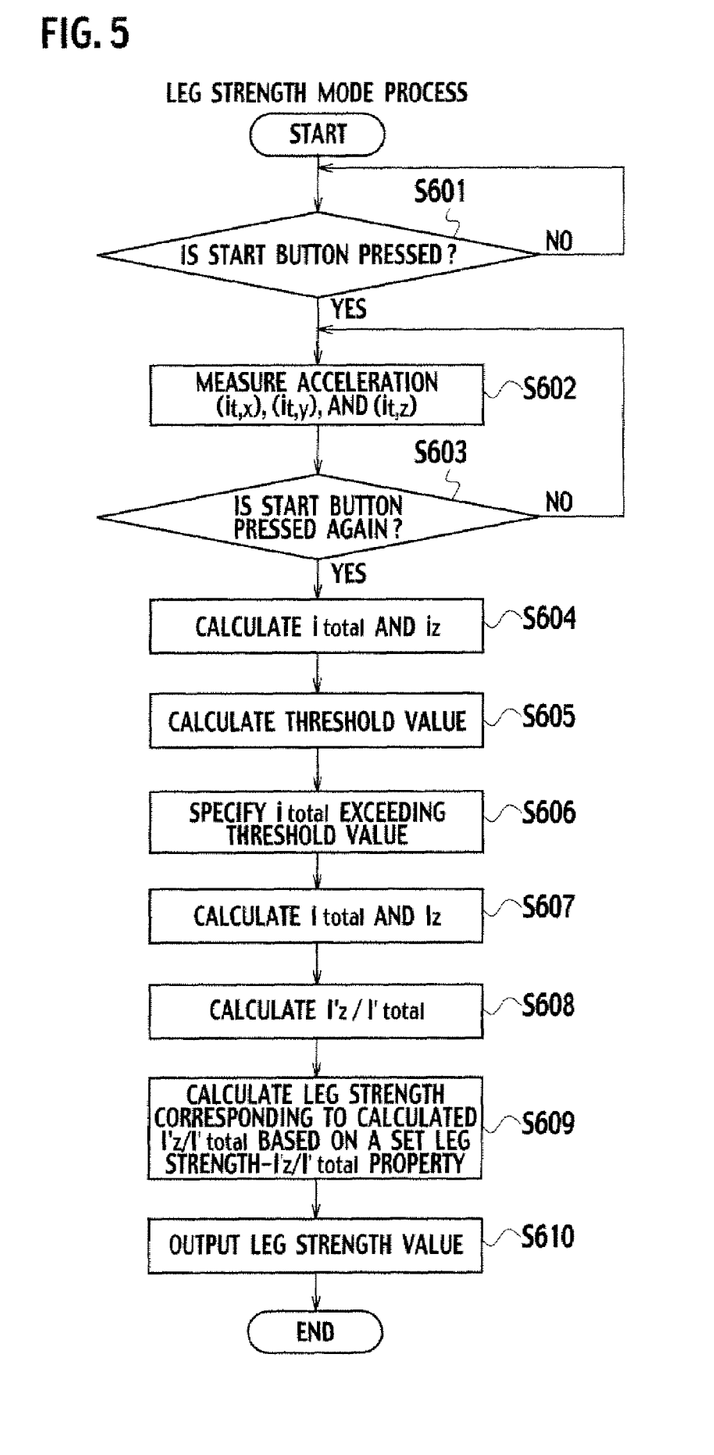
FIG. 5 is a flowchart showing a leg strength mode process according to the first embodiment.

As shown in FIG. 5, in S601, the leg strength calculation device 100 judges whether the start button 103 is pressed down. The leg strength calculation device 100 proceeds to a process of S602 when this judgment is YES and repeats the process of S601 when the judgment is NO.

In step S602, the leg strength calculation device 100 specifies values of three axis acceleration acting on the subject. The three axis acceleration at a time $t=k\Delta T$ is expressed as the following equation. An interval at which a measured value of the acceleration is sampled is indicated by $\Delta T$.

$$\text{Three Axis Acceleration } i \ t = (i_{t,x}, i_{t,y}, i_{t,z}) \qquad \text{Equation 1}$$

Herein, $i_{t,x}$, $i_{t,y}$, and $i_{t,z}$ are the accelerations acting on the subject in the directions of the axes x, y, and z at a time t, respectively.

In S603, the leg strength calculation device 100 judges whether the start button 103 is pressed down again. The leg strength calculation device 100 proceeds to a process of S604 when this judgment is YES and repeats this process of S602 when the judgment is NO.

In S604, the leg strength calculation device 100 calculates impulse $i_{total}$(norm), which is a composite value of impulses acting on the subject in the directions of the three axes from acceleration $i_o$, which is a composite value of the accelerations acting on the subject in the directions of the three axes. The impulse $i_{total}$(norm), which is the composite value of impulses acting on the subject in the directions of the three axes at the time $t=k\Delta T$, is expressed by the following equation. Herein, the weight of the subject is indicated by w.

$$i_{total} = w \cdot io \cdot \Delta T \qquad \text{Equation 2}$$
$$= w \cdot \sqrt{i_{t,x} + i_{t,y} + i_{t,z}} \cdot \Delta T$$

The leg strength calculation device 100 calculates the impulse $i_z$(norm), which is a value of the impulse acting on the subject in the direction of the axis z, based on the acceleration $i_{t,z}$ acting in the direction of the axis z. The impulse $i_z$(norm) acting on the subject in the z-axis direction at the time $t=k\Delta T$ is expressed by the following equation.

$$i_z(t) = w \cdot |i_{t,z}| \cdot \Delta T \qquad \text{Equation 3}$$

Figure 6:
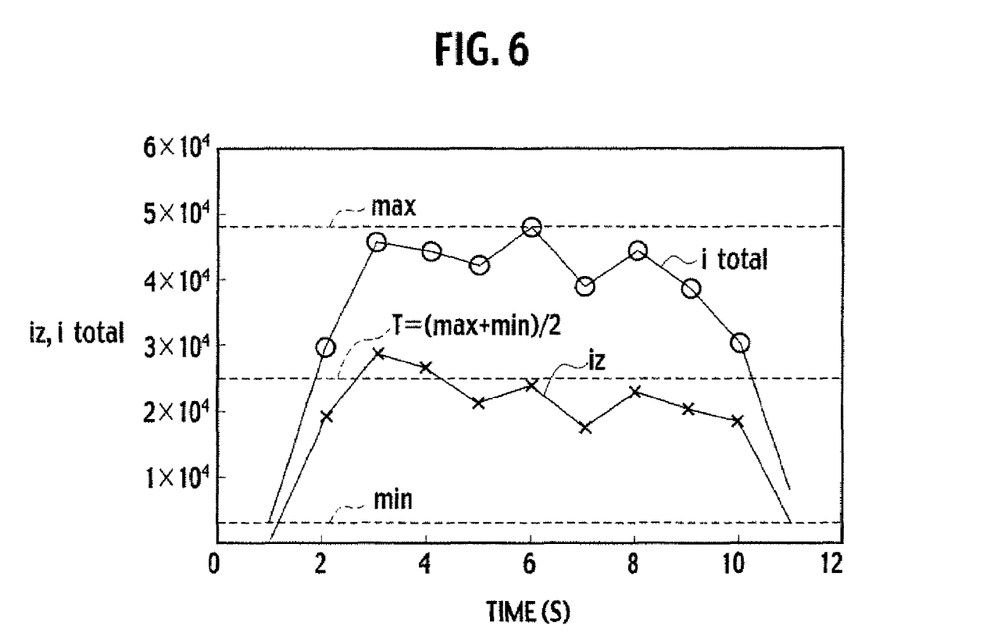
FIG. 6 is a graph showing $i_z$ and $i_{total}$ with respect to measuring time according to the first embodiment.

In S605, the leg strength calculation device 100 sets a threshold value of the impulse $i_{total}$(norm). FIG. 6 is a graph showing the impulse $i_{total}$(norm) and impulse $i_z$(norm) with respect to measuring time.

As shown in FIG. 6, the leg strength calculation device 100 specifies a maximum value (see "max" shown in FIG. 6) and a minimum value (see "min" shown in FIG. 6) of the impulse $i_{total}$(norm). The leg strength calculation device 100 sets the threshold value to the midpoint (see T=(max+min)/2 shown in FIG. 6) between the specified maximum and minimum values of the impulse $i_{total}$(norm).

In S606, the leg strength calculation device 100 specifies values of the impulse $i_{total}$(norm; the measurement composite value) larger than the set threshold value (see round symbols shown in FIG. 6). The leg strength calculation device 100 also specifies values of the impulse $i_z$(norm) at times when the impulse $i_{total}$(norm) exceeds the threshold value (see x symbols shown in FIG. 6).

In S607, the leg strength calculation device 100 calculates average impulse $I_z$(norm) indicating average value of the impulse $i_z$(norm) per unit time and average impulse $I_{total}$(norm) indicating average value of the impulse $i_{total}$(norm) per unit time based on the values of the impulse $i_z$(norm) and impulse $i_{total}$(norm) specified in S606.

Figure 7:
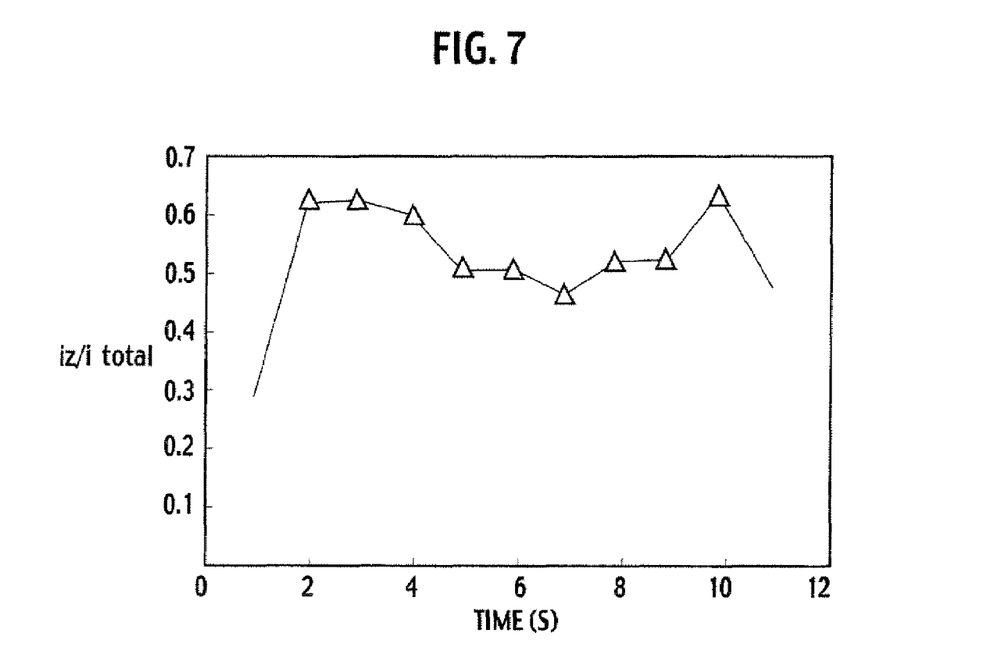
FIG. 7 is a graph showing $i_z/i_{total}$ with respect to the measuring time according to the first embodiment.

The average impulse $I_z$(norm) of the impulse $i_z$(norm) in $n \cdot \Delta T$ and the average impulse $I_{total}$(norm) of the impulse $i_{total}$(norm) in $n \cdot \Delta T$ are expressed by the following equations. FIG. 7 shows the ratio of impulse $i_z$(norm)/impulse $i_{total}$(norm) with respect to measuring time.

$$I_{total} = \frac{\sum_{k=1}^{n} i_{total}(k \cdot \Delta T)}{n \cdot \Delta T} \qquad \text{Equation 4}$$
$$= \frac{w}{n} \sum_{k=1}^{n} \sqrt{(i_{k,x})^2 + (i_{k,y})^2 + (i_{k,z})^2}$$

$$I_z = \frac{\sum_{k=1}^{n} i_z(k \cdot \Delta T)}{n \cdot \Delta T} \qquad \text{Equation 5}$$
$$= \frac{w}{n} \sum_{k=1}^{n} |i_{k,z}|$$

In S608, based on the average impulse $I_z$(norm) and average impulse $I_{total}$(norm) calculated in S607, the leg strength calculation device 100 calculates a ratio of average impulse $I_z$(norm)/average impulse $I_{total}$(norm). The ratio of average impulse $I_z$(norm)/average impulse $I_{total}$(norm) is expressed by the following equation.

$$\frac{I_z}{I_{total}} = \frac{\sum_{k=1}^{n} |i_{k,z}|}{\sum_{k=1}^{n} \sqrt{(i_{k,x})^2 + (i_{k,y})^2 + (i_{k,z})^2}} \qquad \text{Equation 6}$$

Equation 6 also indicates $I_z$(norm)/$I_{total}$(norm) in the period of time $n \cdot \Delta T$. The $I_z$(norm)/$I_{total}$(norm) therefore exists for each period of time $n \cdot \Delta T$. When $n \cdot \Delta T$ is 1 s, for example, $n \cdot \Delta T$ is a period of time between 2 s and 3 s in FIG. 6 and the like.

Accordingly, an average value $I'_z/I'_{total}$ of $I_z$(norm)/$I_{total}$(norm) for a period of time including m times $n \cdot \Delta T$ (for example, the period of time between 2 s and 10 s in FIG. 6) is expressed by the following equation.

$$\frac{I'_z}{I'_{total}} = \frac{1}{m} \sum_{P=1}^{m} \frac{I_{z,P}}{I_{total,P}} \qquad \text{Equation 7}$$

As shown in Equation 7 above, $I'_z/I'_{total}$ is a ratio of an impulse generating the acceleration of the subject in the direction of the axis z to an impulse generating the accelerations of the subject in the three directions of the axes x, y, and z. This $I'_z/I'_{total}$ is largely related to leg strength of the subject.

The smaller this ratio $I'_z/I'_{total}$ is, the less the subject moves up and down in the direction of the axis z while walking at the maximum speed. When the subject has lower leg strength, the walking efficiency is lower, and the subject moves up and down more while walking at the maximum speed.

The ratio $I'_z/I'_{total}$ is thus corresponding to the leg strength of the subject. Accordingly, the approximate expression to estimate the leg strength is given by the following equation. In Equation 8 below, A and B are constants.

$$F = A \cdot \left( \frac{I'_z}{I'_{total}} \right) + B \qquad \text{Equation 8}$$

In S609, the leg strength calculation device 100 assigns $I'_z/I'_{total}$ calculated in S608 to the approximate expression of Equation 8 to calculate leg strength F.

Figure 8:
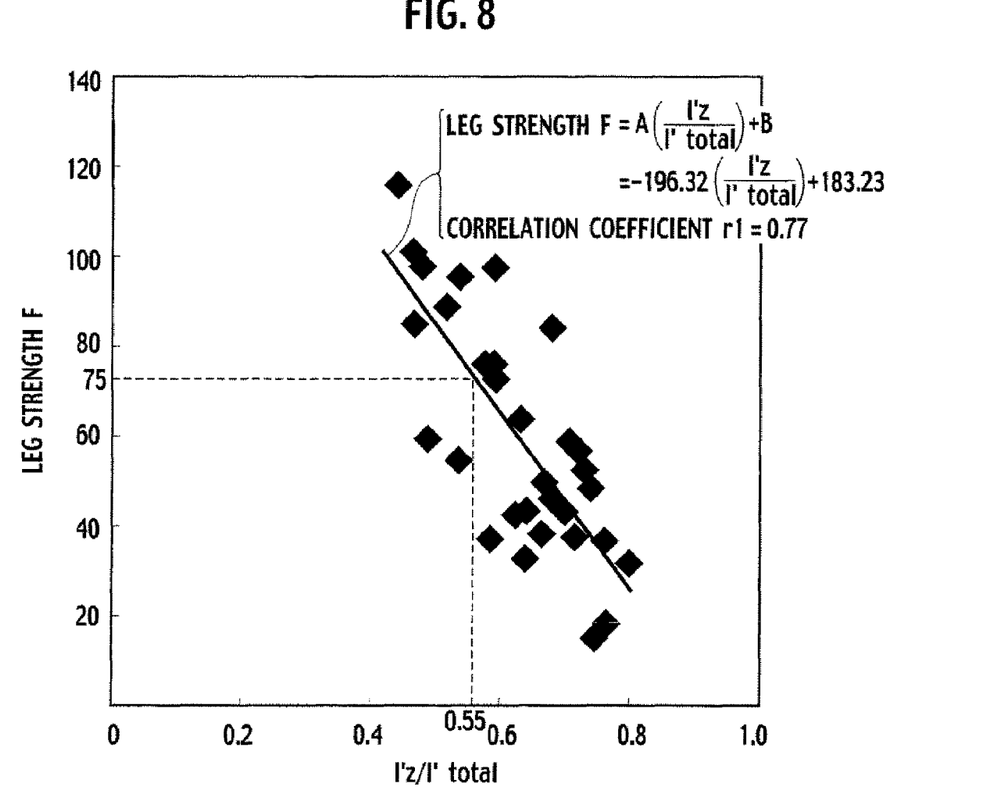
FIG. 8 is a graph showing leg strength with respect to $i'_z/i'_{total}$ according to the first embodiment.

FIG. 8 is a graph showing a leg strength-$I'_z/I'_{total}$ property based on Equation 8 above. In S608, when $I'_z/I'_{total}$ is 0.55, for example, the leg strength calculation device 100 assigns 0.55 to {leg strength $F=A(I'_z/I'_{total})+B$; herein, leg strength $F=-196.32(I'_z/I'_{total})+183.23$} and calculates the leg strength F of the subject as 75.

In S610, the leg strength 100 displays the calculated leg strength F.

Figure 9:
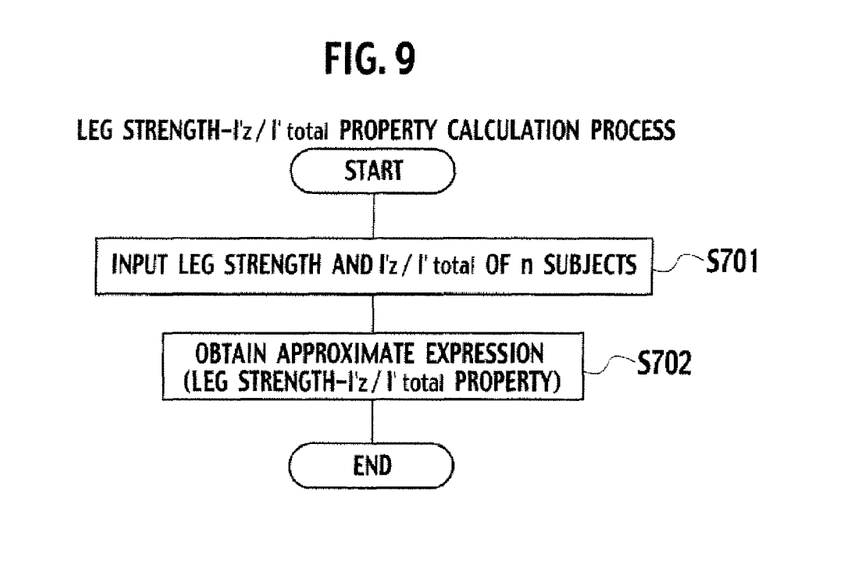
FIG. 9 is a flowchart showing a leg strength-$i'_z/i'_{total}$ property calculation process according to the first embodiment.

Next, with reference to FIG. 9, a description is given of a process to calculate the leg strength-$I'_z/I'_{total}$ property used in S609 above. FIG. 9 is a flowchart showing the process to calculate the leg strength-$I'_z/I'_{total}$ property.

In S701, the leg strength calculation device 100 prompts input of leg strength of a predetermined number (n) of subjects and $I'_z/I'_{total}$ of the predetermined number (n) of subjects when the leg strength thereof is exerted. The predetermined number (n) is such a number that the approximate expression can be calculated by the least square method.

In S702, the leg strength calculation device 100 obtains the approximate expression (see Equation 8 above) using the least square method based on the relation between the inputted values of leg strength of the predetermined number (n) of subjects and $I'_z/I'_{total}$ of the predetermined number (n) of subjects corresponding thereto.

According to the aforementioned characteristic, based on the ratio of $I'_z/I'_{total}$, the leg strength calculation device 100 calculates the leg strength of the subject corresponding to this ratio. The leg strength of the subject can be therefore calculated by subject's walking, which is an exercise that everyone can do, without using exercise equipment which places a large burden on the subject to calculate leg strength thereof.

Moreover, the subject can easily know his/her own leg strength only by wearing the leg strength calculation device 100 without using the large-scale exercise equipment. Furthermore, the leg strength calculation device 100 is small enough to be worn by the subject and not large-scale exercise equipment. Accordingly, the leg strength calculation device 100 can have a structure allowing manufacturing costs to be reduced.

Moreover, the leg strength calculation device 100 can obtain a more proper approximate expression (see Equation 8) using values of $I'_z/I'_{total}$ of a larger number of subjects and values of leg strength of the larger number of subjects. The leg strength calculation device 100 can therefore calculate the leg strength corresponding to $I'_z/I'_{total}$ of a new subject using the approximate expression more accurately.

Moreover, the approximate expression (see Equation 8) does not include an element of weight of the subject. The leg strength calculation device 100 can therefore calculate the leg strength of the subject even when the weight of the subject is not set. Accordingly, the subject does not need to set his/her own weight and can easily know the leg strength of the subject by an easier operation.

Furthermore, the leg strength calculation device 100 uses $I'_z/I'_{total}$ which is calculated by the ratio of the impulse $i_z$ to the impulse $i_{total}$ when the impulse $i_{total}$ exceeds the threshold value, in other words, uses $I'_z/I'_{total}$ calculated by the ratio of the impulse $i_z$ to the impulse $i_{total}$ when the subject is walking at the maximum speed. Accordingly, the leg strength calculation device 100 can calculate the maximum leg strength of the subject based on the ratio.

Moreover, the maximum leg strength of the subject can be calculated just through a distance enough for the subject to walk at the maximum speed without a long distance for measurement of the leg strength of the subject (for example, a long track for walking in an athletic field). Accordingly, the subject can easily measure his/her own maximum leg strength without going to an athletic field or the like.

In this embodiment, the leg strength calculation device 100 previously sets the approximate expression indicating the leg strength-$I'_z/I'_{total}$ property (see S609). The leg strength calculation device 100 is not limited to this and may be modified as follows.

Specifically, the leg strength calculation device 100 sequentially stores values of the leg strength calculated in S610 and values of $I'_z/I'_{total}$ corresponding thereto. When a predetermined number of values of $I'_z/I'_{total}$ and leg strength are stored for a predetermined period of time, the leg strength calculation device 100 obtains the approximate expression using substantially all the stored values of $I'_z/I'_{total}$ and leg strength. The leg strength calculation device 100 replaces the approximate expression previously set with the obtained approximate expression.

In this case, the leg strength calculation device 100 can obtain a more proper approximate expression by sequentially updating the approximate expression based on a larger number of values of $I'_z/I'_{total}$ and leg strength. Accordingly, the leg strength calculation device 100 can more accurately calculate the leg strength corresponding to $I'_z/I'_{total}$ of the subject using the updated approximate expression.

In this embodiment, the leg strength calculation device 100 calculates leg strength of the subject using the approximate expression of the leg strength-$I'_z/I'_{total}$ property but is not limited to this.

Specifically, the leg strength calculation device 100 may calculate leg strength of the subject using a previously set table.

For example, the leg strength calculation device 100 stores a table including a plurality of values of leg strength and a plurality of values of $I'_z/I'_{total}$ associated to each other. After calculating $I'_z/I'_{total}$ of a new subject, the leg strength calculation device 100 specifies a value of the leg strength associated to the calculated value of $I'_z/I'_{total}$ in the table.

The leg strength calculation device 100 calculates leg strength of the subject using $I'_z/I'_{total}$ (see Equations 7 and 8) in the embodiment and modifications but not limited to this. Specifically, the leg strength calculation device 100 may calculate leg strength of the subject using $I_z/I_{total}$ (see Equation 6) instead of $I'_z/I'_{total}$.

In other words, by replacing $I'_z/I'_{total}$ with $I_z/I_{total}$ in Equation 8 and the like, the leg strength calculation device 100 can calculate leg strength corresponding to $I_z/I_{total}$ of a new subject. This can certainly provide similar operations and effects to those in the above description.

The leg strength calculation device 100 may calculate, based on the measurement composite value, which is a composite value of the accelerations acting in the directions of the axes, y, and z and measured by the acceleration sensor 108, and the weight of the subject, the leg strength of the subject corresponding to the measurement composite value and weight.

The leg strength calculation device 100 may calculate leg strength of the subject using $I''_{total}$ shown in Equation 9 below instead of $I'_z/I'_{total}$ (see Equations 7 and 8). $I''_{total}$ includes the measurement composite value and weight (w) (see Equations 4 and 9). The leg strength calculation device 100 can therefore calculate the leg strength of the subject as follows using the measurement composite value and weight (w) included in $I''_{total}$.

$$F = CI''_{total} + D \qquad \text{Equation 9}$$

Following I' total is used in Equation 9

$$I'_{total} = \frac{1}{m}\sum_{P=1}^{m} I_{total,P}$$

Figure 10:
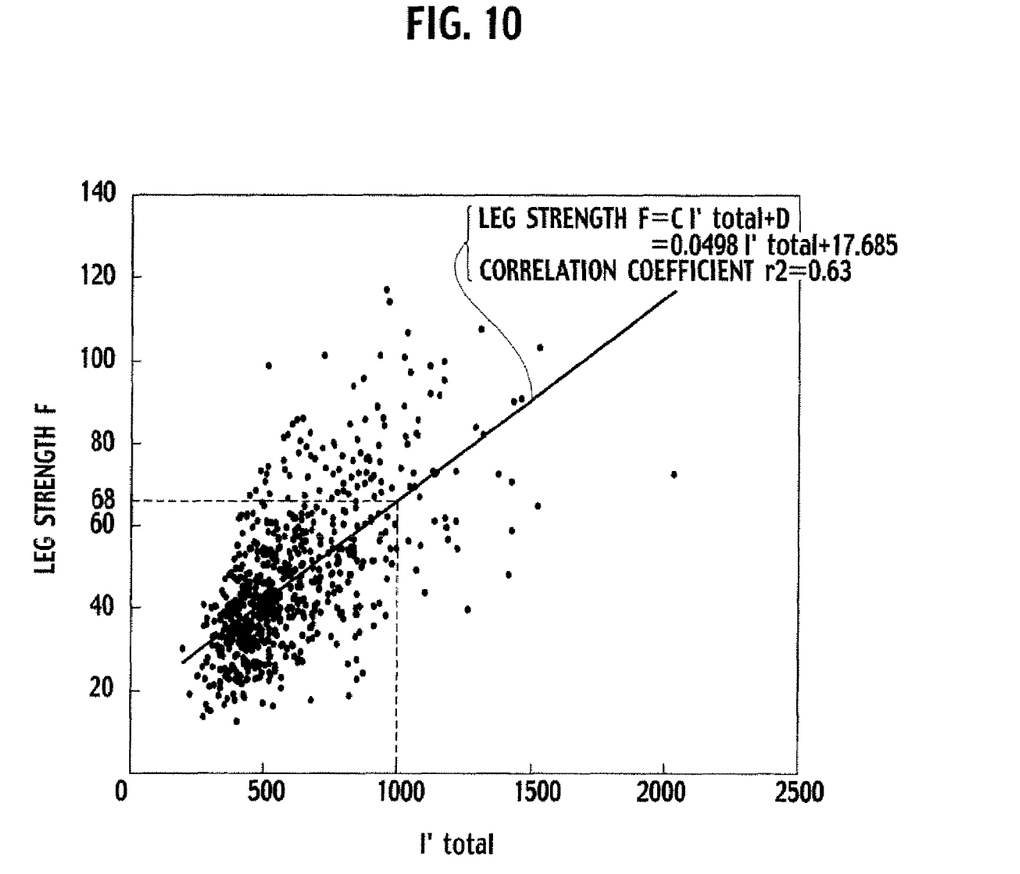
FIG. 10 is a graph showing leg strength with respect to $I'_{total}$ according to a modification.

Herein, FIG. 10 is a graph showing a leg strength-$I'_{total}$ property used to calculate constants C and D in Equation 9 above. The leg strength calculation device 100 calculates the constants C and D in Equation 9 using the least square method based on the relation between the inputted values of the leg strength of the predetermined number (n) of subjects and the corresponding values of $I'_{total}$ of the predetermined number (n) of subjects to obtain the approximate expression of the leg strength F (F=0.0498I'total+17.685; see FIG. 10).

In S608, therefore, when $I'_{total}$ is 1000, for example, the leg strength calculation device 100 assigns 1000 to {leg strength F=0.0498I'total+17.685} to calculate the leg strength F of the subject as about 68.

The leg strength calculation device 100 may calculate, based on the measurement composite value, which is the composite value of the accelerations acting in the directions of the axes x, y, and z and measured by the acceleration sensor 108, leg strength of the subject corresponding to the measurement composite value.

For example, the leg strength calculation device 100 calculates the leg strength of the subject using $I'_{total}/w$ shown in Equation 10 below instead of $I'_z/I'_{total}$. $I'_{total}$ in Equation 10 is $I'_{total}$ in Equation 9.

$I'_{total}$ includes the measurement composite value and weight (w). Accordingly, calculating $I'_{total}/w$ eliminates the element of the weight (w). The leg strength calculation device 100 can calculate the leg strength of the subject as follows using the measurement composite value included in $I'_{total}$.

$$F=EI'_{total}/w+G \quad \text{Equation 10}$$

Figure 11:
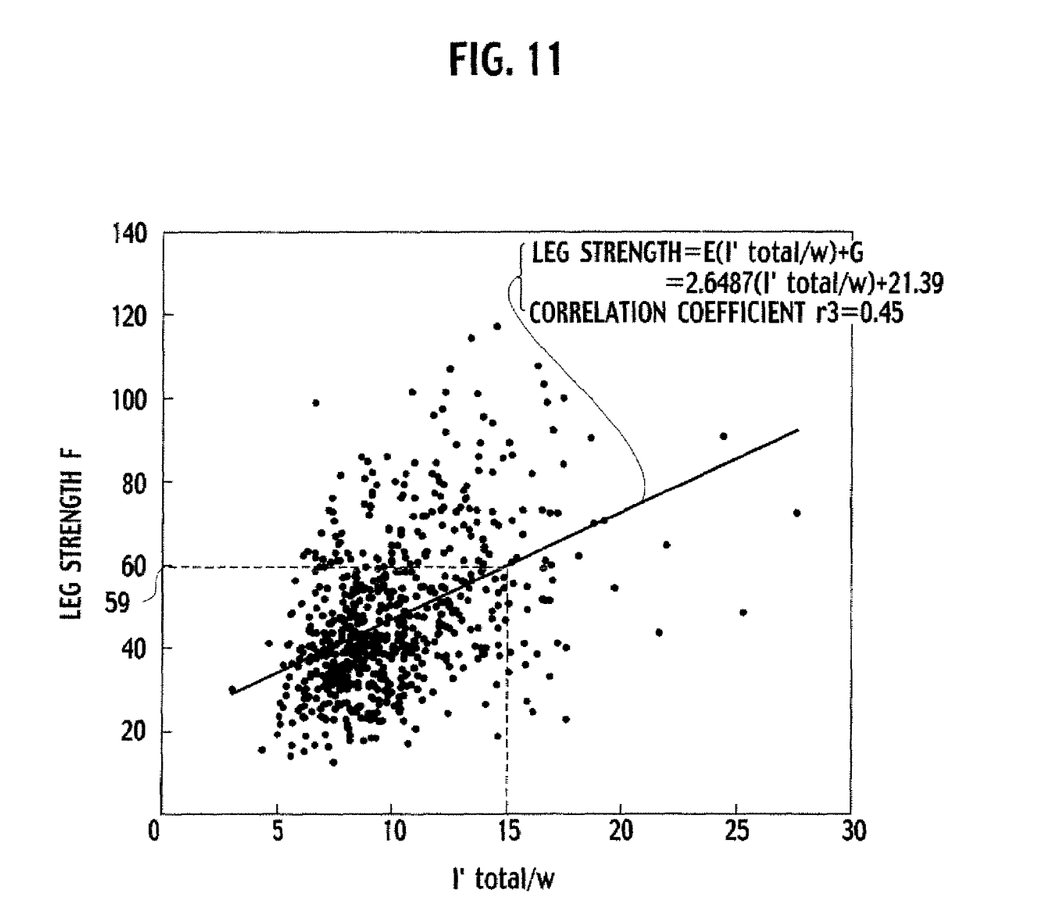
FIG. 11 is a graph showing leg strength with respect to $I'_{total}/w$ according to another modification.

Herein, FIG. 11 is a graph showing a leg strength-$I'_{total}/w$ property used to calculate constants E and G in Equation 10 above. The leg strength calculation device 100 calculates the constants E and G in Equation 10 using the least square method based on the relation between values of the leg strength of the predetermined number (n) of subjects and corresponding values of $I'_{total}/w$ of the predetermined number (n) of subjects to obtain an approximate expression of the leg strength F (F=2.6487$I'_{total}$/w+21.39; see FIG. 11).

In S608, therefore, when $I'_{total}/w$ is 15, for example, the leg strength calculation device 100 assigns 15 to {leg strength F=2.6487I'total/w+21.39} to calculate the leg strength F of the subject as about 61.

Herein, a correlation coefficient r1 calculated from the leg strength F and $I'_z/I'_{total}$ is 0.77 (FIG. 8). A correlation coefficient r2 calculated from the leg strength F and $I'_{total}$ is 0.63 (FIG. 10). A correlation coefficient r3 calculated from the leg strength F and $I'_{total}/w$ is 0.45 (FIG. 11).

The leg strength F and $I'_z/I'_{total}$, the leg strength F and $I'_{total}$, and the leg strength F and $I'_{total}/w$ are corresponding to each other, and using $I'_z/I'_{total}$ $I'_{total}$, or $I'_{total}/w$, the leg strength calculation device 100 can therefore properly calculate the leg strength F corresponding to $I'_z/I'_{total}$ $I'_{total}$, or $I'_{total}/w$.

The leg strength calculation device 100 can execute arithmetic processing of the leg strength F more quickly by using Equation 9 not including a division than by using Equation 8 including a division.

Furthermore, Equation 10 originally does not include the element of the weight. Accordingly, the leg strength calculation 100 can execute the arithmetic processing of the leg strength F more quickly by Equation 10 than by Equation 8 including the element of the weight.

$I'_{total}$ in equations 9 and 10 may be certainly replaced with $I_{total}$.

Second Embodiment

In the first embodiment, the leg strength calculation device 100 calculates the maximum oxygen uptake (endurance) of the subject after causing the subject to increase the walking speed stepwise and walk at the maximum speed that the subject can walk at the final stage (see S200).

On the other hand, in a second embodiment, the leg strength calculation device 100 calculates the maximum oxygen uptake (endurance) of the subject by not causing the subject to increase the walking speed stepwise but causing the subject to walk a particular distance shorter than the walking distance accumulated through each stage in the first embodiment at the maximum speed at which the subject can walk. The structure of each portion in the second embodiment is the same as that of each portion described in the first embodiment if not otherwise specified. Hereinafter, the second embodiment is described in detail.

The leg strength calculation device 100 outputs information prompting the subject to walk a particular distance at the maximum speed at which the subject can walk (see YES in S603 above). After outputting the information, the leg strength calculation device 100 calculates the measurement composite value (a value included in $I'_{total}$ in Equation 9). The measurement composite value is the composite value of accelerations acting in the directions of the axes x, y, and z.

The leg strength calculation device 100 calculates a composite value at maximum exercise intensity. The composite value at maximum exercise intensity includes a composite value of accelerations acting in the directions of the axes x, y, and z when the subject can provide maximum exercise intensity that the subject can, and the weight of the subject. The maximum exercise intensity is the greatest exercise intensity that the subject can make autonomously. This exercise intensity includes the pulse rate, heart rate, caloric expenditure, or oxygen uptake.

For example, the leg strength calculation device 100 calculates $I''_{total}$ including the composite value at maximum exercise intensity using $I'_{total}$ including the calculated measurement composite value and the weight of the subject. The leg strength calculation device 100 calculates the maximum oxygen uptake (endurance) as follows using $I''_{total}$ calculated.

Figure 12:
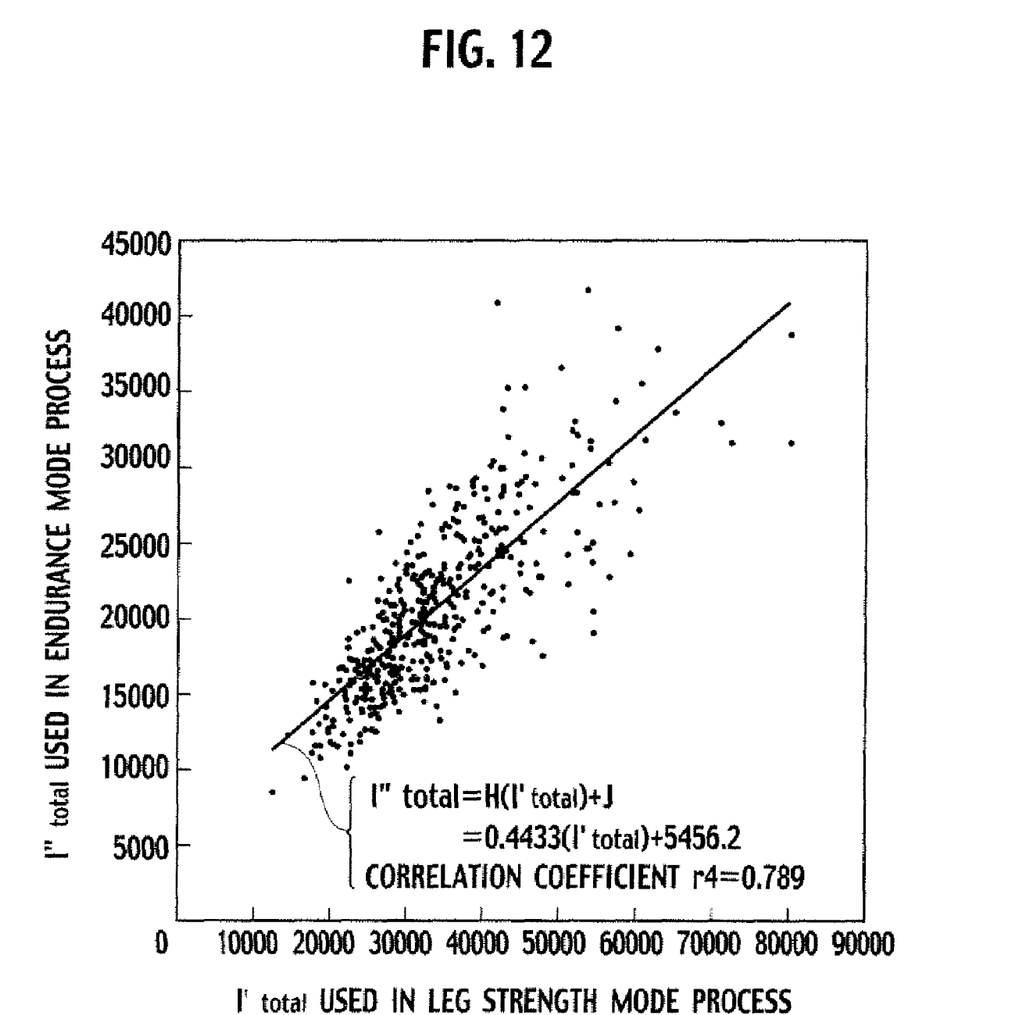
FIG. 12 is a graph showing $I''_{total}$ with respect to $I'_{total}$ according to a second embodiment.

Next, a description is given of a method of calculating the maximum oxygen uptake (endurance) in detail. FIG. 12 is a graph showing a relation between $I'_{total}$ and $I''_{total}$ in the predetermined number (n) of subjects.

As shown in FIG. 12, the leg strength calculation device 100 calculates constants H and J in Equation 11 below using the least square method based on the relation between inputted values of $I'_{total}$ of the predetermined number (n) of subjects and values of $I''_{total}$ of the predetermined number (n) of subjects corresponding thereto to obtain an approximate expression of $I''_{total}$ ($I''_{total}$=0.4433 $I'_{total}$+5456.2; see FIG. 12).

$$I''_{total}=HI'_{total}+J \quad \text{Equation 11}$$

The leg strength calculation device 100 calculates $I''_{total}$ using the approximate expression shown in FIG. 12 and calculated $I'_{total}$. The leg strength calculation device 100 calculates the maximum oxygen uptake (endurance) using the calculated $I''_{total}$ and Equation 12 below.

$$\text{Maximum Oxygen Uptake (Endurance)} = KI''_{total} + L \quad \text{Equation 12}$$

Herein, the leg strength calculation device 100 calculates constant K and L in Equation 12 using the least square method based on the relation between inputted values of $I''_{total}$ of the number (n) of subjects and corresponding values of the maximum oxygen uptake (endurance) of the predetermined number (n) of subjects to obtain an approximate expression of the maximum oxygen uptake (endurance). The process to introduce this approximate expression is the same as the processes described in FIGS. 10, 11, and 12.

The leg strength calculation device 100 can therefore calculate the maximum oxygen uptake (endurance) using the approximate expression shown in Equation 12 and calculated $I''_{total}$.

As shown in FIG. 12, a correlation coefficient r4 calculated from $I''_{total}$ and $I'_{total}$ is 0.789. $I''_{total}$ and $I'_{total}$ are corresponding to each other, and, using only the calculated $I'_{total}$, the leg strength calculation device 100 can properly calculate $I''_{total}$ corresponding to $I'_{total}$.

To calculate the maximum oxygen uptake (endurance), the leg strength calculation device 100 uses $I'_{total}$ or the composite value at maximum exercise intensity included in the same but may certainly use $I_{total}$ or the composite value at maximum exercise intensity included in the same.

The leg strength calculation device 100 calculates the composite value at maximum exercise intensity (dependent on the weight of the subject) using the calculated measurement composite value and the weight of the subject in this embodiment but is not limited to this. Specifically, the leg strength calculation device 100 may calculate the composite value at maximum exercise intensity (independent of the weight of the subject) not using the weight of the subject but using only the calculated measurement composite value.

Third Embodiment

In this embodiment, the leg strength calculation device 100 may execute the following process in addition to the training mode of S400. A structure of each portion of the embodiment is the same as that of each portion described in the first embodiment if not otherwise specified.

Specifically, the leg strength calculation device 100 sets a predetermined proportion (for example, 70%) of the calculated composite value at maximum exercise intensity ($I''_{total}$) as a reference value.

If the composite value at maximum exercise intensity is used as the reference value at training, an excessive load is placed on the subject and can threaten the life of the subject. In terms of exercise physiology, lactic acid begins to be produced when load corresponding to about 60% of the composite value at maximum exercise intensity is placed on the subject. When load corresponding to about 70% thereof is placed on the subject, lactic acid is surely produced. In order to improve the physical strength of the subject, it is necessary that load heavy enough to surely produce lactic acid is placed on the subject. It is therefore preferable that the reference value is set to about 70% of the composite value at maximum exercise value.

The leg strength calculation device 100 outputs physical information related to physical matters of the subject when a measurement composite value (value included in impulse) exceeds the reference value. The measurement composite value is a composite value of the accelerations acting in the directions of the axes x, y, and z measured by the acceleration sensor 108.

For example, the leg strength calculation device 100 outputs physical information when the calculated measurement composite value exceeds the reference value. The physical information indicates that current load is physically proper for the subject.

On the other hand, when the calculated measurement composite value does not exceed the reference value, the leg strength calculation device 100 outputs physical information indicating that the current load is not physically proper for the subject. The physical information indicates that the current load is not physically proper for the subject. The leg strength calculation device 100 can output, for example, a predetermined sound as the physical information from the speaker 105.

According to such a characteristic, when the measurement composite value exceeds the reference value, the physical information is outputted. Accordingly, the subject hears the physical information during exercise and can know that current walking speed is suitable for training of the subject.

Other Embodiment

The leg strength described in each of the aforementioned embodiment may be isometric knee flexion strength measured with knees kept still, isokinetic knee extension strength measured with knees moving, or the like.

The leg extension strength and leg flexion strength as the leg strength of each embodiment, respectively, include knee extension strength and knee flexion strength. The knee extension strength is maximum muscular strength generated when the knees of the subject are extended. The knee flexion strength is maximum muscular strength generated when the knees of the subject are bent.

(Program)

A program operating in the above leg strength calculation device includes functions same as those of the CPU 112. Specifically, the program includes a function as a leg strength calculation unit calculating, based on a ratio of a first acceleration value to a second acceleration value, leg strength of the subject corresponding to the ratio. The first acceleration value is a value of an acceleration of a subject which acts in a direction of an axis z in the vertical direction and is measured by an acceleration sensor. Herein, the acceleration sensor measures accelerations of the subject which act in directions of axes x and y orthogonal to each other and the axis z. The second acceleration value is a composite value of accelerations which act in the directions of the axes of x, y, and z and are measured by the acceleration sensor.

The program may be recorded in a recording medium. This recording medium is a hard disk, a flexible disk, a compact disk, an IC chip, a cassette tape, or the like.

The above description is given of the present invention with the examples. The description just shows concrete examples and does not particularly limit the present invention. The design of a concrete configuration and the like of each portion can be properly changed. Moreover, the configurations of the embodiments and modifications can be properly combined. The aforementioned operations and effects of the embodiments and modifications are just most preferable operations and effects produced by the present invention, and the operations and effects of the present invention are not limited to those described in the aforementioned embodiments and modifications.

What is claimed is:

1. A leg strength calculation device detachably worn by a subject, comprising:

an acceleration sensor configured to measure accelerations of the subject which act in directions of axes x, y, and z orthogonal to each other when the subject walks; and a leg strength calculation unit configured to calculate leg strength of the subject based on values of the accelerations measured by the acceleration sensor.

2. The leg strength calculation device according to claim 1, wherein the axis z is an axis in a vertical direction;

the leg strength calculation unit calculates, based on a ratio of a first acceleration value to a second acceleration value, the leg strength of the subject corresponding to the ratio;

the first acceleration value is a value of the acceleration acting in the direction of the axis z measured by the acceleration sensor; and the second acceleration value is a composite value of the accelerations acting in the directions of the axes x, y, and z measured by the acceleration sensor.

3. The leg strength calculation device according to claim 2, wherein the leg strength calculation unit calculates the leg strength of the subject corresponding to a ratio of the first acceleration value to the second acceleration value based on an approximate expression which is obtained based on a relation between a specific ratio and leg strength of the large number of subjects; and the specific ratio is a ratio of an acceleration acting in the direction of the axis z to a composite value of accelerations acting in the directions of the axes x, y, and z of a large number of subjects.

4. The leg strength calculation device according to any one of claims 2 and 3, wherein the leg strength calculation unit calculates, based on a ratio of the first acceleration value to the second acceleration, the leg strength of the subject corresponding to the ratio value when the second acceleration value is larger than a threshold value.

5. The leg strength calculation device according to claim 1, wherein the leg strength calculation unit calculates, based on a specific value, the leg strength of the subject corresponding to the specific value; and the specific value is a composite value of accelerations acting in the directions of the axes x, y, and z measured by the acceleration sensor.

6. The leg strength calculation device according to claim 1, wherein the leg strength calculation unit calculates, based on a specific value, the leg strength of the subject corresponding to the specific value; and the specific value which includes weight of the subject and a composite value of accelerations acting in the directions of the axes x, y, and z measured by the acceleration sensor.

7. The leg strength calculation device according to any one of claims 5 and 6, wherein the leg strength calculation unit calculates the leg strength of the subject corresponding to the specific value based on an approximate expression which is obtained based on a relation between the specific value of a number of subjects and leg strength of the number of subjects.

8. The leg strength calculation device according to any one of claims 5 to 6, wherein the leg strength calculation unit calculates the leg strength of the subject corresponding to the specific value when the specific value measured is larger than a threshold value.

9. The leg strength calculation device according to claim 1, wherein the leg strength calculation unit calculates a composite value at maximum exercise intensity based on a measurement composite value;

the composite value at maximum exercise intensity is a composite value of the accelerations acting in the directions of the axes x, y, and z when the subject exert the maximum exercise intensity;

the measurement composite value is a composite value of the accelerations acting in the directions of the axes of x, y, and z measured by the acceleration sensor.

10. A method of calculating leg strength using a leg strength calculation device detachably worn by a subject, the method comprising:

a step of measuring accelerations of the subject which act in directions of axes x, y, and z orthogonal to each other when the subject walks; and a calculation step of calculating leg strength of the subject based on values of the accelerations measured.

11. The method of calculating leg strength according to claim 10, wherein the axis z is an axis in a vertical direction;

in the calculation step, the leg strength of the subject corresponding to a ratio is calculated based on the ratio of a first acceleration value to a second acceleration value;

the first acceleration value is a value of the acceleration acting in the direction of the axis z measured; and the second acceleration value is a composite value of the accelerations acting in the directions of the axes x, y, and z measured.

12. The method of calculating leg strength according to claim 11, wherein in the calculation step, the leg strength of the subject corresponding to a ratio of the first acceleration value to the second acceleration value is calculated based on an approximate expression which is obtained based on a relation between a specific ratio and leg strength of the large number of subjects; and the specific ratio is a ratio of an acceleration acting in the direction of the axis z to a composite value of accelerations acting in the directions of the axes x, y, and z of a large number of subjects.

13. The method of calculating leg strength according to any one of claims 11 and 12, wherein in the calculation step, the leg strength of the subject corresponding to a ratio is calculated based on the ratio of the first acceleration value to the second acceleration value when the second acceleration value is larger than a threshold value.

14. The method of calculating leg strength according to claims 10, wherein in the calculation step, the leg strength of the subject corresponding to a specific value is calculated based on the specific value; and the specific value is a composite value of accelerations acting in the directions of the axes x, y, and z measured.

15. The method of calculating leg strength according to claims 10, wherein in the calculation step, the leg strength of the subject corresponding to a specific value is calculated based on the specific value; and the specific value which includes weight of the subject and a composite value of accelerations acting in the directions of the axes x, y, and z measured.

16. The method of calculating leg strength according to any one of claims 14 and 15, wherein
in the calculation step, the leg strength of the subject corresponding to the specific value is calculated based on an approximate expression which is obtained based on a relation between the specific value of a number of subjects and leg strength of the number of subjects.

17. The method of calculating leg strength according to any one of claims 14 to 15, wherein
in the calculation step, the leg strength of the subject corresponding to the specific value is calculated when the specific value measured is larger than a threshold value.

18. The method of calculating leg strength according to claim 10, wherein
in the calculation step, a composite value at maximum exercise intensity is calculated based on a measurement composite value;
the composite value at maximum exercise intensity is a composite value of the accelerations acting in the directions of the axes x, y, and z when the subject exert the maximum exercise intensity;
the measurement composite value is a composite value of the accelerations acting in the directions of the axes of x, y, and z measured by.

19. A program product to be executed by a computer detachably worn by a subject, comprising:
a measurement instruction configured to measure accelerations of the subject which act in directions of axes x, y, and z orthogonal to each other when the subject walks; and
a calculation instruction configured to calculate leg strength of the subject based on values of the accelerations measured.

20. The program product according to claim 19, wherein
the axis z is an axis in a vertical direction;
the calculation instruction is an instruction to calculate, based on a ratio of a first acceleration value to a second acceleration value, the leg strength of the subject corresponding to the ratio;
the first acceleration value is a value of the acceleration acting in the direction of the axis z measured; and
the second acceleration value is a composite value of the accelerations acting in the directions of the axes x, y, and z measured.

21. The program product according to claim 20, wherein
the calculation instruction calculates the leg strength of the subject corresponding to a ratio of the first acceleration value to the second acceleration value based on an approximate expression which is obtained based on a relation between a specific ratio and leg strength of the large number of subjects; and
the specific ratio is a ratio of an acceleration acting in the direction of the axis z to a composite value of accelerations acting in the directions of the axes x, y, and z of a large number of subjects.

22. The program product according to any one of claims 20 and 21, wherein
the calculation instruction calculates, based on a ratio of the first acceleration value to the second acceleration value, the leg strength of the subject corresponding to the ratio when the second acceleration value is larger than a threshold value.

23. The program product according to claim 19, wherein
the calculation instruction calculates, based on a specific value, the leg strength of the subject corresponding to the specific value; and
the specific value is a composite value of accelerations acting in the directions of the axes x, y, and z measured.

24. The program product according to claim 19, wherein
the calculation instruction calculates, based on a specific value, the leg strength of the subject corresponding to the specific value; and
the specific value includes weight of the subject and a composite value of accelerations acting in the directions of the axes x, y, and z measured.

25. The program product according to any one of claims 23 and 24, wherein
the calculation instruction calculates the leg strength of the subject corresponding to the specific value based on an approximate expression which is obtained based on a relation between the specific value of a number of subjects and leg strength of the number of subjects.

26. The program product according to any one of claims 23 to 24, wherein
the calculation instruction calculates the leg strength of the subject corresponding to the specific value when the specific value measured is larger than a threshold value.

27. The program product according to claim 19, wherein
the calculation instruction calculates a composite value at maximum exercise intensity based on a measurement composite value;
the composite value at maximum exercise intensity is a composite value of the accelerations acting in the directions of the axes x, y, and z when the subject exert the maximum exercise intensity;
the measurement composite value is a composite value of the accelerations acting in the directions of the axes of x, y, and z measured.

* * * * *